United States Patent [19]

Minekane

[11] Patent Number: 4,808,380
[45] Date of Patent: Feb. 28, 1989

[54] AUTOMATIC CHEMICAL ANALYZING APPARATUS

[75] Inventor: Tomiharu Minekane, Otawara, Japan
[73] Assignee: Kabushiki Kaisha Toshiba, Kanagawa, Japan
[21] Appl. No.: 17,614
[22] Filed: Feb. 24, 1987
[30] Foreign Application Priority Data Feb. 21, 1986 [JP] Japan .................................. 61-35042

[51] Int. Cl.$^4$ ............................................. G01N 35/04
[52] U.S. Cl. ..................................... 422/64; 422/102; 422/104
[58] Field of Search ...................... 422/64.67, 102, 104, 422/73; 436/45

[56] References Cited
U.S. PATENT DOCUMENTS

| | | |
|---|---|---|
| 4,276,258 | 6/1981 | Ginsberg et al. |
| 4,311,667 | 1/1982 | Gocho ................................. 422/64 |
| 4,325,910 | 4/1982 | Jordan ................................. 422/64 |
| 4,344,768 | 8/1982 | Parker et al. ....................... 422/72 |
| 4,346,056 | 8/1982 | Sakurada . |
| 4,647,432 | 3/1987 | Wakatake ............................ 422/64 |

Primary Examiner—Michael S. Marcus
Attorney, Agent, or Firm—Oblon, Fisher, Spivak, McClelland & Maier

[57] ABSTRACT

An automatic chemical analysis apparatus having a plurality of separate reagent containers placed inside of an annular array of reaction cuvettes. The reagent containers are arranged so as to be selectively accessible for dispensing a required reagent into a respective cuvette. At a predetermined position on the circular path of the cuvette array, a given sample is dispensed from a sample supply into a cuvette. During transporting of the cuvette containing a sample on a reaction path, a reagent from a selected of the reagent containers placed within the annular reaction cuvette array is dispensed by a suitable dispenser which can swing between the annular array of cuvettes and the reagent containers. After the reaction is completed, while the cuvette is advanced in the reaction line, the reactant containers are subjected to a photometric measurement at a measurement station located past the reagent dispensing position on the reaction line. Then the cuvette is returned through a washing station to an original position of the annular reaction line for receiving a new sample.

2 Claims, 1 Drawing Sheet

AUTOMATIC CHEMICAL ANALYZING APPARATUS

FIELD OF THE INVENTION

This invention relates to an apparatus for automatically conducting chemical analytical procedures for monitoring of the absorption of radiant energy by specimens of blood, blood fractions or blood serums which have been treated with certain know reagents. The purpose of such treatment and monitoring is to ascertain the composition of the blood, blood fraction or serum quantitatively with respect to certain chemical constituents.

DISCUSSION OF BACKGROUND

Many automatic chemical analyzing apparata are currently in use, and in particular, automatic chemical analyzing apparata used for clinical tests in hospitals are based on a method in which each sample can be analyzed in terms of a plurality of items and in which samples having different test items are analyzed in such a manner that the test items are automatically changed while continuing the chemical analysis of test items corresponding to new samples.

There are variations in the apparatus associated with the above technique, which, for example, is well known from U.S. Pat. No. 4,346,056 to Sakurada.

A disadvantage of such system is that the reagent supply, which includes a large number of reservoirs containing different reagents to provide greater flexibility so as to be suitable to change test items from sample to sample, occupies considerable space in addition to the space occupied by the cuvette rotor.

Thus, the above machine is somewhat wasteful of the space. In addition, there have been certain problems, such as complexity of the units, cumbersomeness, and cost, associated with the drive mechanism and location mechanism for the large size reagent supply to position the programmed reagent into position aligned with the movement of a pick up and dispensing probe for picking up the reagent and moving and dispensing it into the cuvette of the cuvette rotor.

SUMMARY OF INVENTION

Accordingly, the object of the present invention are to provide a new and improved automatic chemical analyzing apparatus which has relatively simple components, is reliable in operation, and is compact, thus assuring that everything is done efficiently and with complete identification as a result of which a maximum number of tests can be done in a minimum amount of time.

Another object of this invention is to provide an automatic chemical analyzing apparatus having a large number of reagent containers arranged in a small space, thereby to provide an analyzing apparatus having reduced size and capable of efficiently dispensing the necessary reagent(s) for the respective test items assigned to the programmed cuvette.

These and other objects are achieved according to the invention by providing an automatic chemical analysis apparatus including a circular array carrying a plurality of cuvettes in which the samples are dispensed and mixed with reagent(s) and which are then analyzed by a photometer, and a reagent ring having separate reagent containers placed into respective cavities on a rotor arranged coaxial and concentric with the array of cuvettes within the array of cuvettes.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

Figure 1:
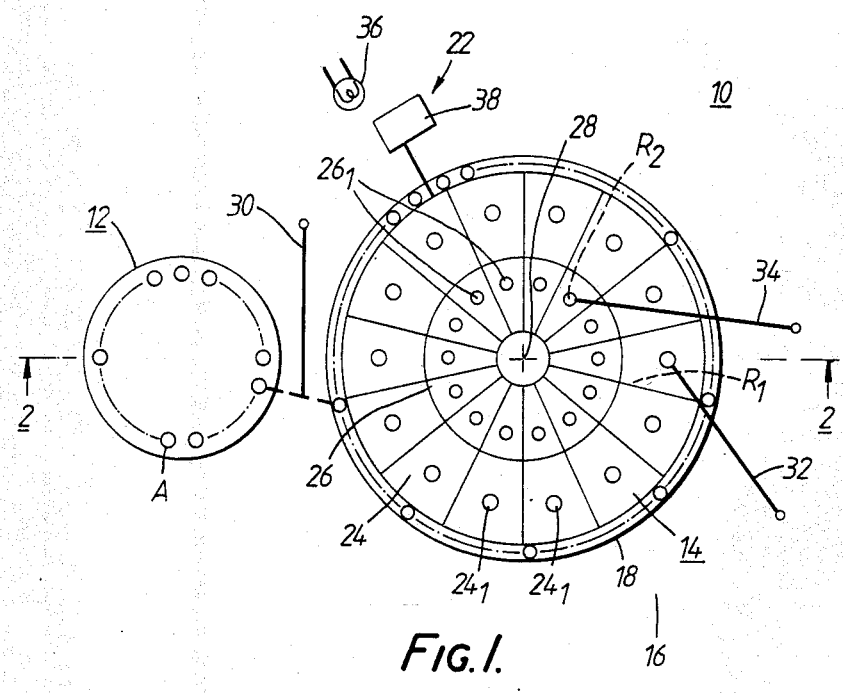
FIG. 1 is a top plan view of an apparatus in accordance with the present invention.

Referring now to the drawings, wherein like reference numerals designate identical or corresponding parts throughout the several views, and referring particularly to FIG. 1, the automatic chemical analyzing apparatus of the present invention is indicated by the reference numeral 10. The apparatus can be composed of a master control unit (not shown), which has many functions including processing of input information supplied from suitable data input means (not shown) concerning each sample and the different chemical tests to be performed on aliquots of each specific sample, and providing each unit with commands pertinent to each of the chemical tests that the apparatus 10 is capable of performing. The complete ambit of control performed by the master control is well known to those skilled in the art and is therefore not discussd in more detail.

The major units of the apparatus 10 include a sample supply 12 and a reagent supply 14. The samples from the supply 12 and reagents from the reagent supply 14 are transferred to and observed in a chemical reaction analyzer 16.

The analyzer 16 includes a cuvette rotor 18 in which cuvettes 20 are mounted in an annular array in a turntable. The sample aliquots are dispensed into the specific cuvettes 20, mixed with reagent, and then analyzed by a photometer 22.

During its complete circuit of movement for a single revolution of the rotor 18, any given cuvettes 20 will have had its mixture subjected to fluid processing, chemical reaction, and measurement, and as well will be prepared to receive a new sample for the repetition of the cycle. The cuvettes array will be indexed forward one step for each cuvette and its associated aliquot. As used herein, "step" and "indexed" include but are not limited to discrete movements, since the cuvette array could be continuously slowly moving.

The reagent supply area 14 has a pair of coaxial reagent rings 24 and 26 each of which have a plurality of separate reagent containers $24_1$ and $26_1$ in each reagent ring.

The reagent supply area 14 is placed peripherally within the ring of the cuvette array and rotates on the axis 28 which is also the axis of rotation of the cuvette rotor 18, and each reagent ring 24, 26 is separately controlled and driven for greater flexibility. The mounting and driving means for the reagent rings 24 and 26 will be described with reference to FIG. 2.

A sample dispenser 30, forms of which are known, can accomplish the transferring, with each required chemical test being associated with an identified cuvette 20 for that specific sample. First and second reagent dispensers 32 and 34 pick up appropriate reagents from the respective reagent rings 24 and 26, and transfer and dispense into specific cuvettes 20 as those cuvettes advance around the path of movement of the annular array.

Such transfer dispensers 30, 32, and 34 swing arcuately between the source of fluid 12, 24 or 26 and a cuvette 20. Both when receiving and dispensing fluid the probe of the dispensers 30, 32 and 34 can move down into the containers, but are elevated to be able to swing free thereof in arcuate paths R1 and R2.

Between the time and position that the sample is dispensed and the first reagent is dispensed there is a distance along the path of movement of the annular array of the cuvettes during which photometric measurement is made by the photometer 22. Photometer 22 includes a source of radiation such as a lamp 36 and radiation detector 38 which can be photoelectric cells, photomultipliers or the like. The lamp 36 and the radiation detector 38 are both located outside of the path followed by the circular array of cuvettes, and the radiation detector 38 receives the transmitted radiant energy through the cuvette which is reflected by a suitable reflecting means (not shown) disposed below the cuvette array 18.

Figure 2:
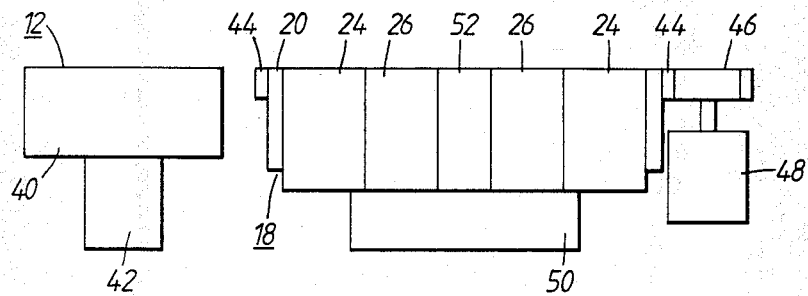
FIG. 2 is a diagrammatic cross-sectional view taken generally along the line 2—2 of FIG. 1 and in the indicated direction, portions being shown in elevation.

Referring now to FIG. 2, the drive mechanism and locating mechanism for the sample supply 12 and reagent rings 24 and 26, and the rotating mechanism for the cuvette rotor 18 are illustrated. The sample supply 12 has a mounting disc 40 on which a tray (not shown) including an ordinary sample container array loaded with the samples to be analyzed in a plurality of cavities is mounted. The mounting disc 40 is mounted and connected to a drive shaft which is rotated by a motor 42 so that these sample containers are adapted to be transferred to the transferring position with respect to the sample dispenser 30 by rotation of the disc 40, as required.

The reaction analyzer 16 includes a temperature-maintained annular path (not shown) and the cuvette rotor 18 arranged thereon. The cuvette rotor 18 has a multiplicity of holes each loaded with the reaction cuvette 20 of a transparent cell, thus forming an cuvette array. Some part of the reaction cuvette is immersed in the temperature-maintained atmosphere. On the outer periphery of the rotor 18 there is provided a geared rack 44 engaged with a gear wheel 46 driven by a motor mounted on the base (not shown). The motor is connected by suitable leads to the control unit which provides the necessary commands and power to drive the motor 48 so that the rotor 18 is properly positioned and moved for the purposes of the apparatus.

The first reagent ring 24 is mounted to a rotating shaft (not shown) by a suitable means, and the rotating shaft is rotated about a stationary shaft 52 which is mounted to the base plate. The shaft is spaced from the stationary shaft by an appropriate bearing, and the ring 24 and its shaft are rotated by a motor 50 mounted to the base plate. The position of the ring 24 with respect to its dispensing position on the arc R1 is controlled by the control unit based upon reading a bar or other machine readable code applied to the respective reagent containers of which identification is read by a suitable reader device (not shown). The second inner reagent ring 26 is mounted on a concentric shaft with the shaft for the first reagent ring 24. The concentric shaft is spaced from and revolves about the stationary shaft by a bearing (not shown). The shaft for the second reagent ring 26 also has a drive transferring mechanism which is driven by a motor (not shown) similar to the motor 50. The positioning of the second inner reagent ring 26 is also under control of the control unit reading the identification issued to the respective containers placed on the second inner ring 26. Preferably the cuvette rotor 18 is disposed as high as the reagent rings. The reagent rings 24 and 26 are arranged rotatably and respectively inside of the cuvette array of the rotor 18.

As mentioned previously, the apparatus of the invention has great flexibility in being applicable to many testing choices. Test selection is achieved by the apparatus by carrying out chemical analysis for the samples to be dispensed into the cuvettes successively corresponding to programmed test items under control of the master control unit. In this type of automatic chemical analyzer in which a multiplicity of analysis items are analyzed selectively with respect to each sample, a plurality of reagents may be required, and different reagent containers must be moved to the dispensing position in the path of movement of the dispensing probe so that a desired reagent can be transferred from a selected reagent container to the given cuvette depending on an item to be analyzed.

In operation, the sample dispensing probe 30 sucks and holds the sample at the position where the sample to be analyzed is positioned so as to be under the arcuate path of the probe of dispenser 30 and discharges the held sample at the discharge point on the reaction path defined by the cuvette array by swinging the probe of dispenser 30. The array of the reaction cuvette 20 is transferred to cross the measurement light path from the source 36 and the cuvette rotor 18 makes one revolution plus one step so that the cuvette next to the one that has received the sample is positioned at the discharge position. This sampling operation is continuously repeated.

In this way, the cuvette rotor 18 makes one rotation and one step for each specimen sampling process, while the reaction cuvette 20 that has contained the sample for the first time reaches the first reagent discharge position where the circular path of the annular array of cuvettes crosses the arcuate path of movement of the probe of the first reagent dispenser 32. The probe of the first reagent dispenser probe 32 sucks a reagent solution corresponding to the analysis item from the selected reagent container $24_1$, placed into the rotatable ring 24. This ring 24 is rotated under computer control during which time the bar code applied to each container is read. While holding the solution, the probe of the dispenser 32 moves to the first reagent discharge point on the circular path of the cuvete array 20 where the reagent is discharged into the cuvette 20. The sample in the cuvette chemically reacts and present a color when the reagent is added thereto.

After discharge of the first reagent, when the first reaction cuvette 20 reaches the second discharge position where the path of the cuvette rotor 18 crosses the arcuate path of the probe of the second reagent dispenser 34, the second reagent dispenser 34 dispenses a second different reagent, if required, according to the analysis item.

These reagent distribution operations are similar but independent of the first reagent distribution made to the previous sample.

Next, the reaction cuvette 20 is rotated to the photometer 22 where the cuvette 20 directly receives a light beam from the lamp 36. The light transmitted through the cuvette is subjected to a light absorption by the reaction mixture contained in the cuvette 20 and the amount of light transmitted through the cuvette 20 is sensed by the radiation 38. The radiation detector 38 responds to the amount of radiation transmitted through the reaction mixture in the cuvette and the cuvette walls by generating an electric signal proportional to such amount of radiation. A suitable data processor (not shown) connected to the detector 38 provides an electric signal which is proportional to the transmittance of the reaction mixture, and the absorbance of the sample.

The apparatus 10 which is shown utilizes a reagent distributor ring rotatably disposed inside the cuvette array. It therefore is smaller and more compact than the conventional apparatus, thereby lessening the distance between the reagent container and the cuvettes to which the required reagent is to be dispensed. This allows a relatively slow movement of the dispensing probe without a complex positioning mechanism to produce alignment of the dispensing probe and the cuvettes, and without sacrificing economy or throughout.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. An automatic chemical analysis apparatus consisting essentially of:
   a plurality of reaction cuvettes each adapted to contain a sample to be analyzed, each sample corresponding to a predetermined test item, said cuvettes arranged in an annular array;
   means for advancing said reaction cuvettes successively along a reaction line defined by said annular cuvettes array;
   a plurality of reagent containers each containing a different reagent solutoin, said reagent containers being mounted on concentric turntables disposed concentrically inside of said cuvettes array;
   means for dispensing a selected reagent directly from a selected of any of said reagent containers mounted on said concentric turntables to a selected reaction cuvette of the annular array surrounding said selected reagent container in correspondence to the test item of the sample contained in the selected cuvette when said selected cuvette is positioned at a reagent dispensing position; and
   photometric means disposed adjacent said annular array which concentrically surrounds said concentric turntables on which said reagent containers are mounted for optically measuring the reaction products of each of said plurality of reaaction cuvettes.

2. An apparatus according to claim 1, comprising:
   said reagent containers arranged in the form of at least one ring which is concentric about axis of rotation of the annular cuvette array and is rotatable independently of the rotation of said cuvette array inside of said cuvette array.

* * * * *